United States Patent
Best et al.

(10) Patent No.: US 6,312,468 B1
(45) Date of Patent: Nov. 6, 2001

(54) SILICON-SUBSTITUTED APATITES AND PROCESS FOR THE PREPARATION THEREOF

(75) Inventors: Serena Michelle Best, Ridgmont; William Bonfield, Welwyn; Iain Ronald Gibson, Aberdeen, all of (GB); Lakhan Jee Jha, Ashiyana Nagar (IN); Jose Domingos Da Silva Santos, Leca Do Balio (PT)

(73) Assignee: Abonetics Limited, London (GB)

( * ) Notice: Subject to any disclaimer, the term of this patent is extended or adjusted under 35 U.S.C. 154(b) by 0 days.

(21) Appl. No.: 09/147,733

(22) PCT Filed: Aug. 29, 1997

(86) PCT No.: PCT/GB97/02325

§ 371 Date: Aug. 9, 1999

§ 102(e) Date: Aug. 9, 1999

(87) PCT Pub. No.: WO98/08773

PCT Pub. Date: Mar. 5, 1998

(30) Foreign Application Priority Data

Aug. 30, 1996 (GB) .................................................. 9618175

(51) Int. Cl.⁷ .............................. A01F 2/28; C01B 25/32; C04B 12/02; C09C 1/02
(52) U.S. Cl. ...................... 623/16.11; 106/462; 106/690; 423/308; 423/309; 423/311
(58) Field of Search ..................................... 423/308, 309, 423/311; 623/16.11; 106/690, 462

(56) References Cited

FOREIGN PATENT DOCUMENTS

| 0 115 549 A | 8/1984 | (EP) . |
| WO95 02886 A | 1/1995 | (WO) . |

OTHER PUBLICATIONS

Tanizawa et al., Phosphorous Research Bulletin, 4: 83–88 (1994). (no month).
Kouju et al., Bokin Bobai–Journal of Antibacterial and Antifungal Agents, 23(2): 67–71 (1995). (no month).
Ruys, J. Aust. Ceram. Soc., 29(1 / 2): 71–80 (1993). (no month).
Boyer et al., European Workshop on Transformation Kinetics and Reactivity of Solids (Eurosolid), Louvain La Neuve, Belgium, 95(1–2): Nov. 30–Dec. 1, 1995; Solid State Ionics, Diffusion & Reactions, Elsevier, Netherlands, 121–129, Feb. 1997.
Leshkivich et al., Journal of Materials Science, 28(1): 9–14 (1993). (no month).
Chemical Abstracts, 117(6): Aug. 10, 1992 (Kouju et al. & Gypsum Lime).
Chemical Abstracts, 110(25): Jun. 19, 1989 (Michihiro et al. & Gypsum Lime).
Chemical Abstracts, 122(14): Apr. 3, 1995 (Takashi et al. & JP 06 277 673A).
Chemical Abstracts 110: 230604. (no date).*

* cited by examiner

Primary Examiner—Wayne Langel
(74) Attorney, Agent, or Firm—Bacon & Thomas

(57) ABSTRACT

The present invention provides a synthetic silicon-substituted apatite or hydroxyapatite which comprises 0.1% to 5% by weight of silicon. The silicon-substituted apatite or hydroxyapatite may be used as a synthetic bone material for use in bone substitution, implants, fillers and cements, coatings for metallic implants, and for making hydroxyapatite-polymer composites. The silicon-substituted apatite is prepared by reacting a calcium salt or calcium hydroxide with orthophosphoric acid or a salt of orthophosphoric acid in the presence of a silicon-containing compound, the molar ratio of calcium ions to phosphorous-containing ions being from 1:0.5 to 1:0.7 and the molar ratio of calcium ions to silicon-containing ions being at least 1:0.2, whereby a precipitate of a silicon-substituted apatite is formed. On heating and/or sintering the silicon-substituted apatite at a temperature of from 500° C. to 1400° C. part or substantially all of the silicon-substituted apatite transforms to silicon-substituted hydroxyapatite.

26 Claims, 1 Drawing Sheet

SILICON-SUBSTITUTED APATITES AND PROCESS FOR THE PREPARATION THEREOF

Figure 1:
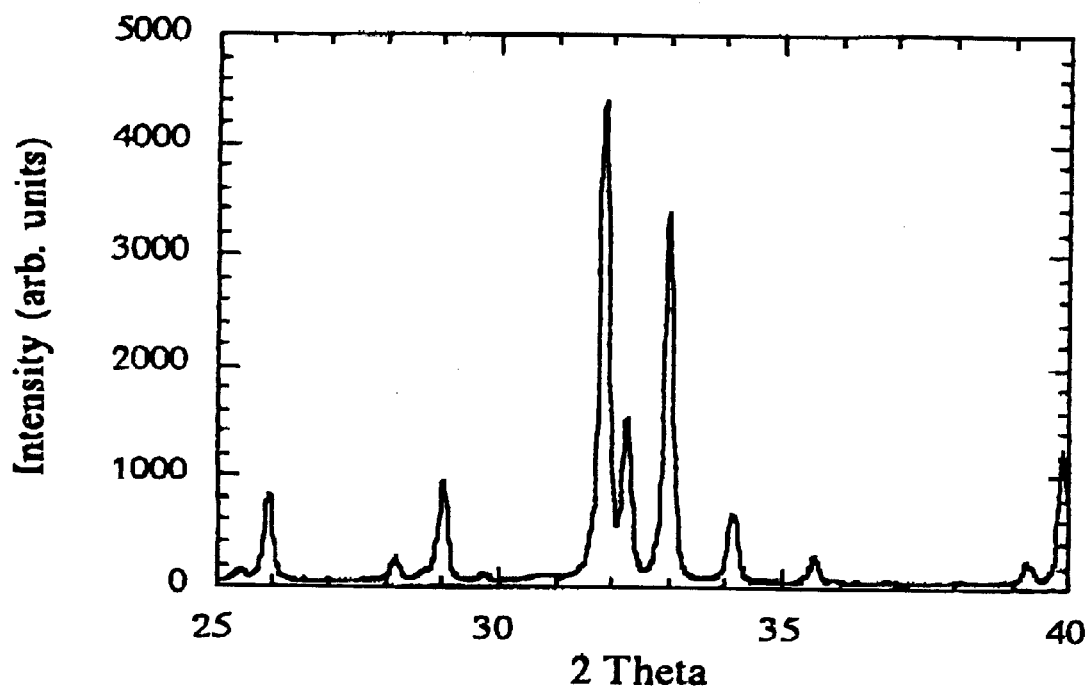

The present invention relates to a silicon-substituted apatite and to a process for the preparation thereof.

The apatite group of minerals are based on calcium phosphate, with naturally occurring apatite having a molar ratio of Ca/P of 1.67. Hydroxyapatite, which has the chemical formula $Ca_{10}(PO_4)_6(OH)_2$, and hydroxyapatite—glass composites have been used in the recent past as skeletal reconstitution materials and it has been observed that bonding of these bioactive materials to living tissues is achieved through a bone-like apatite layer formed on their surfaces in a body environment. Formation of a bone-like apatite layer on implant material thus plays a vital role in osseointegration of the implant.

K. Hata et al., J. Am. Ceram. Soc., 78, 1049–1053 (1995) have shown that a bone-like apatite layer is formed on the surfaces of CaO and $SiO_2$ glass-ceramics in simulated body fluid. It is suggested by the authors that the mechanism of formation of the apatite layer comprises the dissolution of calcium and silicate ions from the glass surface which helps the formation of an apatite layer with silicate ions providing nucleation sites. Another mechanism proposed by Hench et al., J. Biomed. Mater. Res., 2, 117, 1971 is that the pH of the surface of the implant becomes alkaline due to dissolution of ions which in turn causes supersaturation resulting in the precipitation of a bone-like apatite layer. Other mechanisms have also been suggested, including the proposal by Li et al., J. Mater. Sci. Mater. Med., 3, 452, 1992, that dissolution of amorphous calcium phosphate from the glass creates a negatively charged surface which attracts calcium ions to the implant surface and finally forms an apatite layer.

Silicate sulphate apatite has been synthesised by a solid state method, K. S. Leshkivich et al., J. Mater. Sci. Mater. Med., 4, 86–94, 1993, and found excellent biocompatability in vivo tests and this material has been suggested for use as a low-load bearing bone graft material.

Silicon has been shown, in small quantities, to have a significant effect on the development and growth of the hard tissue of living bodies.

EP-A-0 540 819 relates to calcium phosphate and calcium carbonate materials with antibacterial properties, in which these materials are used as a carriers for silver and silicon. JP-A-7165518 relates to an antibacterial inorganic powder. JP-A-7008550 relates to a hydroxyapatite material for use in surgical replacement which contains Ba, Bi, Zr, Sr or Si to improve X-ray contrast. JP-A-60024848 relates to a tooth or bone repair composition comprising a mixture of apatite derived from the bones of fish or mammals and an oxide of Zr, Al, Si and Zn.

We have now developed a silicon-substituted apatite material which has a much higher bioactivity than that of pure hydroxyapatite and which may be used as a synthetic bone material.

Accordingly, the present invention provides a synthetic silicon-substituted apatite or hydroxyapatite which comprises from 0.1 to 5% by weight of silicon. By the term silicon-substituted is meant that silicon is substituted into the apatite crystal lattice and is not merely added, in contrast to the prior art. It is believed that the silicon enters the lattice on the phosphate site. The silicon is though to exist and/or substitute as a silicon ion or as a silicate ion.

The silicon-substituted apatite or hydroxyapatite material according to the present invention may be an essentially single phase pure material.

Preferably, the synthetic silicon-substituted apatite or hydroxyapatite comprises from about 0.1 to about 1.6%, more preferably from about 0.5 to about 1.0% by weight of silicon.

The present invention also provides for the preparation of a stoichiometric silicon-substituted apatite which, when heated and optionally sintered at a temperature of from about 500° C. to 1400° C., for example at about 1200° C., produces an essentially single phase material with a crystal structure comparable to pure hydroxyapatite. The present invention therefore allows for the production of an essentially phase pure material of silicon-substituted hydroxyapatite, which contains substantially no impurity phases, such as calcium oxide or tricalcium phosphate (TCP).

The silicon-substituted apatite or hydroxyapatite material may be used as a synthetic bone material, including dental materials, for example for use in bone substitution, implants, fillers and cements, coatings for metallic implants, and for making hydroxyapatite-polymer composites.

In another aspect the present invention provides a process for the preparation of a silicon-substituted apatite, which process comprises reacting a calcium salt or calcium hydroxide with orthophosphoric acid or a salt of orthophosphoric acid in the presence of a silicon-containing compound, the molar ratio of calcium ions to phosphorous-containing ions being from about 1:0.5 to about 1:0.7 and the molar ratio of calcium ions to silicon-containing ions being at least about 1:0.2, whereby a precipitate of a silicon-substituted apatite is formed. Under these conditions it is believed that the silicon-containing compound yields silicon-containing ions, such as silicon ions and/or silicate ions for example, which substitute in the apatite lattice.

The molar ratio of calcium ions to phosphorous ions is preferably from about 1:0.55 to about 1:0.65 and the molar ratio of calcium ions to silicon ions is preferably at least about 1:0.16.

The process of the present invention is advantageously carried out by reacting an aqueous solution comprising a calcium salt or calcium hydroxide and a silicon-containing compound at a pH of from about 9 to about 13 with an aqueous solution comprising a salt of orthophosphoric acid at a pH of from about 9 to about 13. The calcium salt is preferably calcium nitrate and, in particular, calcium nitrate 4-hydrate. The salt of orthophosphoric is preferably diammonium orthophosphate or triammonium orthophosphate. The pH of the aqueous solution of the calcium salt and/or the pH of the aqueous solution of the salt of orthophosphoric acid is preferably adjusted using ammonia, for example concentrated aqueous ammonia. The preferred pH of each solution is about pH 11.

An alternative way of carrying out the process of the present invention comprises reacting an aqueous solution of calcium hydroxide and a silicon-containing compound with an aqueous solution of orthophosphoric acid. The pH of the aqueous solution of calcium hydroxide is preferably from about 10 to about 14, more preferably about 12.3. The pH of the aqueous solution of orthophosphoric acid is preferably from about 1 to about 3, more preferably from about 1 to about 1.5.

In each of the embodiments of the process of the invention the silicon-containing compound preferably comprises a silicon salt, such as a silicon carboxylate. Advantageously the silicon-containing compound comprises silicon acetate and, in particular, silicon acetate 4-hydrate.

The precipitated silicon-substituted apatite may be separated from the reaction mixture by, for example, filtration, and then washed and dried to result in a silicon-substituted apatite material. The dried filter cake material may then be powdered using conventional techniques.

The dried silicon-substituted apatite material may then be heated and optionally sintered using conventional techniques, for example at a temperature of about 1200° C. Upon heating, the silicon-substituted apatite material transforms to a silicon-substituted hydroxyapatite material, although some of the material may decompose to a mixture of hydroxyapatite and calcium oxide or hydroxyapatite and tricalcium phosphate (TCP), depending on the chemical composition of the material. If formed, then preferably substantially all of the TCP is α TCP. Ideally, little or no decomposition of the silicon-substituted apatite material occurs upon heating, thereby resulting in an essentially phase pure material of silicon-substituted hydroxyapatite. A phase purity, as measured by X-ray diffraction, of at least 98% can be achieved, preferably at least 99%, more preferably approximately 100%. Because certain phases, for example TCP, are soluble in body fluids, a high phase purity is beneficial to the long-term stability of the material. It will be appreciated, however, that a range of materials containing silicon-substituted hydroxyapatite in varying amounts may be prepared in accordance with the present invention depending on the concentrations of the various reactants. For example, two phase materials comprising silicon-substituted hydroxyapatite and TCP or calcium oxide can still usefully be used and are intended to fall within the scope of the present invention.

The present invention will now be described further, by way of example, with reference to the following drawing, in which:

FIG. 1 shows the distribution of X-ray intensity for the hydroxyapatite material of Example 6 (discussed below).

The present invention will be further described with reference to the following Examples.

EXAMPLE 1

141.69 g of calcium nitrate 4-hydrate was dissolved in 600 ml of double distilled water. The pH of solution was adjusted to about 11.0 using a concentrated ammonia solution. 1200 ml of double distilled water was then added to the solution. The solution was filtered. 8.46 g of silicon acetate 4-hydrate was added to the constantly stirred calcium nitrate solution. The solution was heated at about 65° C. for about one hour, with stirring. Most of the silicon acetate 4-hydrate dissolved in the solution and only a very little remained suspended in the solution. The solution was constantly stirred and cooled down to the pre-determined temperature of the experiment. The solution was named as Solution A.

47.54 g of diammonium hydrogen orthophosphate was dissolved in 360 ml of double distilled water. The pH of the solution was adjusted to about 11 using a concentrated ammonia solution. 480 ml of double distilled water was then added to the constantly stirred solution. The solution was filtered. The solution was named as Solution B.

Solution B was added dropwise to constantly stirred Solution A at the predetermined temperatures of 3°, 25°, 60° and 90° C. over a period of about 2 hours. The precipitates so formed (A,B,C and D, respectively) were each agitated at room temperature for one hour and left overnight. Each precipitate was filtered using a Buchner funnel and washed several times using double distilled water. The filter cakes were dried for about 20 hours in a drier at about 85° C. in filtered air. The dried materials were powdered using a pestle and mortar.

The microstructures of the precipitates were studied using a JEOL 100 CX transmission electron microscope (TEM). Carbon coated 200 mesh copper grids were dipped in a dilute suspension of the precipitate and examined in the bright field mode at a magnification of 50000× using an accelerating voltage of 100 kV. The TEM micrographs indicated that the precipitate had a spheroidal shape when precipitated at 3° C. and an increasingly acicular shape when precipitated at 60° and 90° C.

X-ray diffraction studies of powdered samples were performed using a Siemens D5000 diffractometer. $CU_{K\alpha}$ radiation ($K_\alpha$=1.5418 Å) was used with a linear position sensitive detector and a nickel diffracted beam monochromator.

Fourier transform infrared Nicolet 800 spectrometer (FTIR) with a Mtech photoacoustic (PAS) cell was used to analyse the powered samples. Spectra were obtained at 4 $cm^{-1}$ resolution averaging 128 scans. The FTIR spectra of the samples precipitated at 3° and 25° C. showed phosphate bands at 1085, 1030, 961, 600 and 563 $cm^{-1}$, carbonate bands at 1455, 1418, 1327 and 883 $cm^{-1}$ and a hydroxyl band at 3567 $cm^{-1}$ with a broad peak.

A GBC Integra XM sequential inductively coupled plasma spectrometer (ICPS) was used to analyse for calcium, phosphorous, silicon and other trace elements in the prepared apatites. The carbonate content in the dry powder of silicon substituted apatite was determined as carbon using a Control Equipment Corporation Model 240 XA CHN element analyser. The results are given in Table 1 below:

TABLE 1

| Sample | Ca mg/kg | P mg/kg | Si mg/kg | Mg mg/kg | Na mg/kg | Al mg/kg | Fe mg/kg | Cu mg/kg | Ba mg/kg | Sr mg/kg | Carbonate mg/kg |
|---|---|---|---|---|---|---|---|---|---|---|---|
| A | 450800 | 185200 | 10146 | 15.4 | 4.98 | 27.8 | 25.8 | 1.1 | <0.2 | 65.5 | 12500 |
| B | 408800 | 181300 | 10748 | 67.5 | 24.0 | 21.3 | 22.2 | <1.0 | 2.2 | 61.1 | 8000 |
| C | 417700 | 176200 | 8820 | 4.4 | 10.6 | 15.4 | 23.5 | 2.6 | <0.2 | 66.3 | 7000 |
| D | 463100 | 182100 | 10330 | 3.4 | 18.7 | 22.5 | 26.7 | 2.1 | <0.2 | 68.1 | 9000 |
| HA at 3° C. | 35400 | 181000 | 34.0 | 18.2 | 106 | 13.6 | <1.0 | 3.2 | 1.6 | 66.2 | 10000 |
| HA at 90° C. | 344000 | 179000 | 81.5 | 17.8 | 54.9 | 155.0 | <1.0 | 4.8 | 1.4 | 56.0 | 7000 |

HA = hydroxyapatite

EXAMPLE 2

The procedure of Example 1 was repeated, using an amount of 4.23 g of silicon acetate 4-hydrate. Precipitation was again carried out at temperatures of 30, 25°, 60° and 90° C. to form precipitates A, B, C and D.

The precipitates were subjected to ICPS analysis, and the results are given in Table 2 below:

TABLE 2

| Sample | Ca mg/kg | P mg/kg | Si mg/kg | Mg mg/kg | Na mg/kg | Al mg/kg | Fe mg/kg | Cu mg/kg | Ba mg/kg | Sr mg/kg | Carbonate mg/kg |
|---|---|---|---|---|---|---|---|---|---|---|---|
| A | 458200 | 191400 | 4526 | 7.8 | 191 | 23.6 | 20.0 | <1.0 | 0.3 | 60.8 | 9000 |
| B | 469700 | 194200 | 4188 | <1.0 | 30.4 | 20.2 | 33.3 | 1.2 | <0.2 | 64.5 | 6000 |
| C | 433400 | 186600 | 4429 | 3.1 | 30.3 | 22.0 | 44.9 | 2.0 | <0.2 | 64.6 | 6000 |
| D | 454700 | 185500 | 4820 | 1.8 | 44.9 | 28.6 | 25.9 | <1.0 | <0.2 | 65.3 | 7000 |

EXAMPLE 3

The procedure of Example 1 was repeated, using amounts of 1.06 g and 12.69 g of silicon acetate 4-hydrate, respectively. The precipitations were carried out at 3° C. to give precipitates A and B, respectively.

The precipitates were subjected to ICPS analysis and the results are given in Table 3 below:

TABLE 3

| Sample | Ca mg/kg | P mg/kg | Si mg/kg | Mg mg/kg | Na mg/kg | Al mg/kg | Fe mg/kg | Cu mg/kg | Ba mg/kg | Sr mg/kg | Carbonate mg/kg |
|---|---|---|---|---|---|---|---|---|---|---|---|
| A | 424000 | 252000 | 1883 | 0.9 | 55.3 | 37.6 | 12.1 | 1.0 | <0.1 | 63.6 | 11500 |
| B | 393000 | 268000 | 16101 | 10.3 | 64.9 | 10.5 | 24.6 | 0.8 | 3.6 | 67.9 | 16500 |

EXAMPLE 4

44.46 g of calcium hydroxide was dissolved in 600 ml of double distilled water. 0.564 g of silicon acetate 4-hydrate was dissolved in the calcium hydroxide solution. The solution was named as Solution A.

38.02 g of orthophosphoric acid was dissolved in 360 ml of double distilled water. The solution was named as Solution B.

Solution B was added dropwise to solution A over a period of about 2 hours at a temperature of about 3° C. The precipitate so formed, designated precipitate A, was stirred for 1 hour and left overnight. Precipitate A was filtered using a Buchner funnel and washed several times using double distilled water. The filtered cake was dried for about 20 hours in a drier at about 85° C. in filtered air. The dried material was powdered using a pestle and mortar.

This procedure was repeated, using amounts of 2.82, 5.64 and 8.46 g of silicon acetate 4-hydrate. The precipitations were again carried out at about 3° C. to give precipitates B, C and D, respectively.

The precipitates A, B, C and D were subjected to ICPS analysis and the results are given in Table 4 below:

TABLE 4

| Sample | Ca mg/kg | P mg/kg | Si mg/kg | Mg mg/kg | Na mg/kg | Al mg/kg | Fe mg/kg | Cu mg/kg | Ba mg/kg | Sr mg/kg | Carbonate mg/kg |
|---|---|---|---|---|---|---|---|---|---|---|---|
| A | 424000 | 244000 | 814 | 41.0 | 48.4 | 17.5 | 24.6 | 0.5 | 2.6 | 2.9 | 50000 |
| B | 433000 | 240000 | 2957 | 31.4 | 115.3 | 18.8 | 27.1 | <0.5 | <0.1 | 2.1 | 45000 |
| C | 395000 | 250000 | 5337 | 27.5 | 54.7 | 22.3 | 28.4 | 0.8 | <0.1 | 4.5 | 60000 |
| D | 390000 | 271000 | 5634 | 23.7 | 27.1 | 10.8 | 31.6 | <0.5 | <0.1 | 2.0 | 110500 |

EXAMPLE 5

The silicon-substituted apatite material of Example 2A was pressed and sintered at about 1200° C. at a heating rate of about 2.5° C./minute and a dwell time of about 4 hours at the final temperature. The sintered sample was polished with diamond paper and a mirror-like surface was obtained. Hydroxyapatite was also pressed and sintered under the same conditions.

The samples were soaked in a simulated body fluid. After 1 day, thin film X-ray diffraction spectra indicated that the sintered silicon substituted apatite material of Example 2A had formed a bone-like apatite layer, whereas the sintered hydroxyapatite formed a similar layer only after immersion in the fluid for 14 days.

EXAMPLE 6

36.671 g of calcium hydroxide was dissolved in 1000 ml of double distilled water. 1.917 g of silicon acetate 4-hydrate was dissolved in the calcium hydroxide solution. The solution was named as Solution A.

33.331 g of orthophosphoric acid (GPR 85% assay) was dissolved in 1000 ml of double distilled water. The solution was named as Solution B.

Solution B was added dropwise to Solution A over a period of about 2 hours at a temperature of approximately 20° C. The pH of the mixture was adjusted to approximately 10.5 using a concentrated ammonia solution. The precipitate so formed, designated precipitate A, was stirred for 1 hour and left overnight. Precipitate A was filtered using a Buchner funnel and washed several times using double distilled water. The filtered cake was dried at about 85° C. in filtered air. The dried material was powdered using a pestle and mortar.

The powder was then subjected to chemical analysis and the results are given in Table 5 below.

Next, the powder was heated at approximately 1200° C. for about 2 hours and the phases present were determined using X-ray diffraction. With reference to FIG. 1, the heated powder contained only one phase which matched the standard diffraction pattern for pure hydroxyapatite (Joint Committee for Powder Diffraction Standards, JCPDS Card no. 9-432).

The lattice parameters of the heated silicon-substituted hydroxyapatite were calculated from the diffraction data using a least squares refinement method. The values are listed in Table 6, along with the values for pure hydroxyapatite prepared by the above method, with 0.5 moles of $Ca(OH)_2$ and 0.3 moles of $H_3PO_4$, which does not contain any silicon. The increase in the lattice parameters is evidence of the substitution of silicon in the hydroxyapatite lattice.

TABLE 5

| Sample | Ca mg/kg | P mg/kg | Si mg/kg | Mg mg/kg | Na mg/kg | Al mg/kg | Fe mg/kg | Cu mg/kg | Ba mg/kg | Sr mg/kg | Carbonate mg/kg |
|---|---|---|---|---|---|---|---|---|---|---|---|
| A | 381600 | 171900 | 3410 | 15 | 65 | 21 | 32 | 2 | 0.2 | 62 | 5000 |

TABLE 6

|  | a-axis (nm) | c-axis (nm) |
|---|---|---|
| Pure hydroxyapatite | 0.94159 (1) | 0.68798 (1) |
| Single phase silicon-substituted hydroxyapatite prepared in accordance with the invention | 0.94208 (2) | 0.68889 (2) |

What is claimed is:

1. An essentially phase-pure synthetic silicon-substituted hydroxyapatite material comprising from 0.1% to 1.6% by weight of silicon and having substantially no impurity phases of calcium oxide and/or tricalcium phosphate.

2. An essentially phase-pure synthetic silicon-substituted hydroxyapatite material as claimed in claim 1 having a phase purity, as measured by X-ray diffraction, of at least 98%.

3. An essentially phase-pure synthetic silicon-substituted hydroxyapatite material as claimed in claim 2 having a phase purity, as measured by X-ray diffraction, of at least 99%.

4. An essentially phase-pure synthetic silicon-substituted hydroxyapatite material as claimed in claim 3 having a phase purity, as measured by X-ray diffraction, of approximately 100%.

5. An essentially phase-pure synthetic silicon-substituted hydroxyapatite as claimed in claim 1 comprising from 0.5% to 1.0% by weight of silicon.

6. A synthetic bone material comprising an essentially phase-pure synthetic silicon-substituted hydroxyapatite material as claimed in claim 1.

7. A composition which comprises a synthetic bone material as claimed in claim 6 together with a pharmaceutically acceptable diluent or carrier.

8. A bone implant, filler or cement which comprises a synthetic bone material as claimed in claim 6.

9. A hydroxyapatite-polymer composite material comprising a synthetic bone material as claimed in claim 6.

10. A bone implant, filler or cement which comprises a composition as claimed in claim 7.

11. A hydroxyapatite-polymer composition material comprising a composition as claimed in claim 7.

12. An essentially phase-pure synthetic silicon-substituted hydroxyapatite material as claimed in claim 1 comprising from 0.5% to 1.6% by weight of silicon.

13. A process for the preparation of a silicon-substituted hydroxyapatite material, which process comprises:
(i) reacting a calcium salt or calcium hydroxide with orthophosphoric acid or a salt of orthophosphoric acid in the presence of a silicon-containing compound, the molar ratio of calcium ions to phosphorous-containing ions being from 1:0.5 to 1:0.7 and the molar ratio of calcium ions to silicon-containing ions being at least 1:0.2, whereby a precipitate of a silicon-substituted apatite is formed, and
(ii) heating and/or sintering the silicon-substituted apatite, whereby part or substantially all of the silicon-substituted apatite transforms to silicon-substituted hydroxyapatite.

14. A process as claimed in claim 13, wherein the silicon-substituted apatite is heated and/or sintered at a temperature of from 500° C. to 1400° C.

15. A process as claimed in claim 13, wherein the molar ratio of calcium ions to phosphorous-containing ions is from 1:0.55 to 1:0.65.

16. A process as claimed in claim 10, wherein the molar ratio of calcium ions to silicon-containing ions is at least 1:0.16.

17. A process as claimed in claim 10, wherein an aqueous solution of a calcium salt and a silicon compound at a pH of from 9 to 13 is reacted with an aqueous solution comprising a salt of orthophosphoric acid at a pH of from 9 to 13.

18. A process as claimed in claim 10, wherein the calcium salt comprises calcium nitrate.

19. A process as claimed in claim 10, wherein the salt of orthophosphoric acid comprises diammonium orthophosphate.

20. A process as claimed in claim 14, wherein the pH of the aqueous solution of the calcium salt and/or the pH of the aqueous solution of the salt of orthophosphoric acid is adjusted using ammonia.

21. A process as claimed in claim 20, wherein the pH of each solution is adjusted to approximately 11.

22. A process as claimed in claim 10, wherein an aqueous solution comprising calcium hydroxide and a silicon-containing compound is reacted with an aqueous solution comprising orthophosphoric acid.

23. A process as claimed in claim 10, wherein the silicon-containing compound comprises a silicon carboxylate.

24. A process as claimed in claim 23, wherein the silicon carboxylate comprises silicon acetate.

25. A process as claimed in claim 10, wherein the precipitated silicon-substituted apatite is separated from the solution and dried prior to being heated and/or sintered.

26. A process as claimed in claim 10, wherein the precipitated silicon-substituted apatite material comprises from 0.1% to 1.6% by weight of silicon, which material when heated and/or sintered transforms into an essentially phase-pure synthetic silicon-substituted hydroxyapatite material having substantially no impurity phases of calcium oxide and/or tricalcium phosphate.

* * * * *